United States Patent [19]

Söder et al.

[11] 4,182,624

[45] Jan. 8, 1980

[54] IMIDAZOLE CARBOXYLIC ACIDS AND DERIVATIVES THEREOF

[75] Inventors: Alfons Söder, Frankfurt am Main; Hermann Bieringer, Eppstein; Helmut Bürstell, Frankfurt am Main; Peter Langelüddeke, Hofheim am Taunus; Burkhard Sachse, Kelkheim, all of Fed. Rep. of Germany

[73] Assignee: Hoechst Aktiengesellschaft, Frankfurt am Main, Fed. Rep. of Germany

[21] Appl. No.: 925,546

[22] Filed: Jul. 17, 1978

[30] Foreign Application Priority Data

Jul. 19, 1977 [DE] Fed. Rep. of Germany ....... 2732531

[51] Int. Cl.² ............................................... A01N 9/22
[52] U.S. Cl. ............................................ 71/92; 544/82; 544/139; 546/210; 548/317; 548/336; 548/343
[58] Field of Search ............... 548/343, 317, 336; 546/210; 544/82, 139; 71/92

[56] References Cited

U.S. PATENT DOCUMENTS

| | | | |
|---|---|---|---|
| 2,519,310 | 8/1950 | Dessert | 548/317 |
| 3,547,942 | 12/1970 | Godefroi et al. | 548/343 |
| 3,711,487 | 1/1973 | Draber et al. | 548/336 |
| 3,852,056 | 12/1974 | Draber et al. | 548/336 |
| 3,993,647 | 11/1976 | Wenzelburger et al. | 548/336 |
| 4,018,924 | 4/1977 | Buchel et al. | 544/139 |
| 4,020,064 | 4/1977 | Wade et al. | 544/82 |
| 4,038,286 | 7/1977 | Roevens et al. | 548/343 |
| 4,118,461 | 10/1978 | Miller et al. | 548/336 |

FOREIGN PATENT DOCUMENTS

| | | | |
|---|---|---|---|
| 1184709 | 7/1959 | France | 548/343 |
| 1367746 | 6/1963 | France | 548/317 |

OTHER PUBLICATIONS

Chem. Abstracts, 84:4853n.

*Primary Examiner*—Ethel G. Love
*Attorney, Agent, or Firm*—Curtis, Morris & Safford

[57] ABSTRACT

Benzhydryl-imidazole derivatives having carboxyl functions in the imidazole ring have valuable properties in plant protection and growth regulation in agriculture and horticulture. They are also effective as antimycotis, fungicides and herbicides and can be used for combating plant-pathogenic bacteria.

12 Claims, No Drawings

IMIDAZOLE CARBOXYLIC ACIDS AND DERIVATIVES THEREOF

German Offenlegungsschrift No. 2,130,673 describes benzhydrylimidazole derivatives carrying alkyl substituents in the imidazole ring. 1-Benzyl- and 1-tetrahydronaphthyl-imidazole (5)-carboxylic acids and their esters are also known (J. Med. Chem. 15, 336–337 (1972)). Benzhydryl-imidazole derivatives having carboxyl functions in the imidazole ring have not yet become known.

It has now been found that compounds of this type have valuable properties in plant protection and growth regulation.

The present invention therefore provides compounds of the formulae

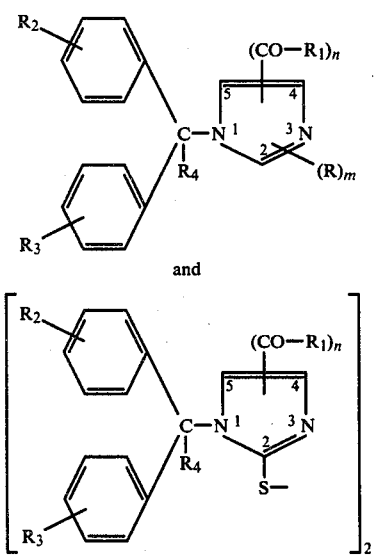

in which
m is zero, 1 or 2,
n is 1 or 2, and
m+n is equal to or smaller than 3;
R is halogen, $(C_1-C_6)$alkyl, allyl, hydroxy$(C_1-C_6)$alkyl, halo$(C_1-C_6)$alkyl, thiol, $(C_1-C_6)$alkylthio, cyano, phenyl or phenyl$(C_1-C_2)$alkyl;
$R_1$ is hydroxy, $(C_1-C_6)$alkoxy, hydroxy$(C_2-C_6)$alkoxy, $(C_2-C_6)$alkoxyalkoxy, di$(C_1-C_3)$alkylphosphinyl-$(C_1-C_3)$alkoxy, di$(C_1-C_3)$alkylphosphinyl-$(C_2-C_3)$hydroxyalkoxy, amino, $(C_1-C_6)$alkylamino, di$(C_1-C_6)$alkylamino, di$(C_1-C_3)$alkylamino$(C_1-C_3)$alkylamino, hydroxyamino, $(C_1-C_3)$alkoxyamino; N-$(C_1-C_3)$-alkyl-N-$(C_1-C_3)$-alkoxyamino, anilino, N-pyrrolidino, N-piperidino, N-morpholino, hydrazino, N'-$(C_1-C_3)$-alkylhydrazino, N',N'-dimethylhydrazino or N'-phenylhydrazino,
$R_2$ and $R_3$, which may be identical or different, are hydrogen, halogen, $(C_1-C_3)$alkyl, trifluoromethyl, hydroxy, $(C_1-C_3)$alkoxy, halo $(C_1-C_3)$alkoxy, $(C_1-C_3)$alkylthio, cyano, nitro or acetamino, and
$R_4$ is hydrogen or phenyl,
and the non-toxic salts thereof with acids or bases.

In the compounds of formulae I and II preferred halogens are chlorine or bromine. The salts of the compounds are preferably the acid salts with mineral acids such as nitric acid, hydrochloric acid, sulfuric acid, or phosphoric acid, or alkali metal (Na, K) or ammonium salts. Alkaline earth metal salts or salts with organic bases such as triethylamine are also effective.

The compounds according to the invention can be prepared by a great variety of processes, for example by
(a) reacting a compound of the formula

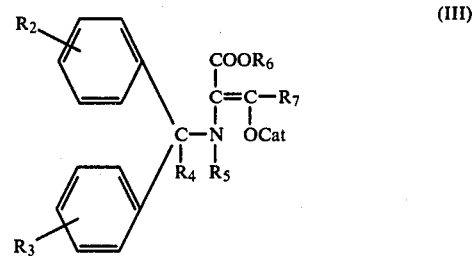

in which
$R_5$ is formyl or acetyl
$R_6$ is $(C_1-C_6)$alkyl
$R_7$ is hydrogen or $(C_1-C_6)$alkoxycarbonyl and Cat is an alkali metal cation, with thiocyanic acid and, if desired, in the 2-thio-imidazole of the formula

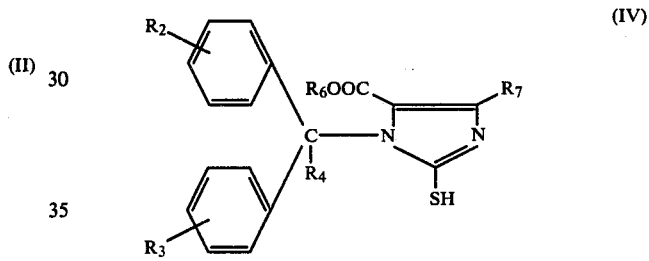

(a$_1$) dehydrating the SH group in 2-position of the imidazole ring to form a —S—S—(disulfide) bridge or
(a$_2$) eliminating the SH-group in 2-position of the imidazole ring by desulfurization, optionally followed by halogenation or hydroxy-methylation in 2-position, or
(b) reacting a compound of the formula

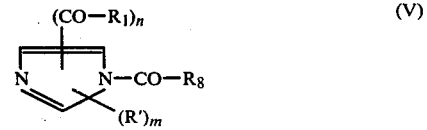

in which $R_8$ is hydrogen or $(C_1-C_3)$alkyl and R' has the meaning of R except that R' is not a —SH group, with a compound of the formula

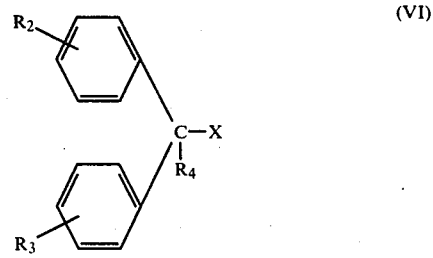

in which X is halogen or an alkyl or arylsulfonyl group and then splitting off the group —CO—R$_8$ in known manner, or (c) reacting a compound of the formula

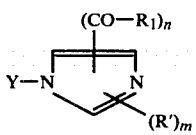
(VIII)

in which Y is hydrogen, an alkali metal or a silver atom with a compound of the formula VI, or (d) reacting a compound of the formula

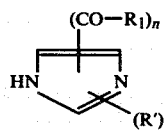
(VIII)

with a compound of the formula

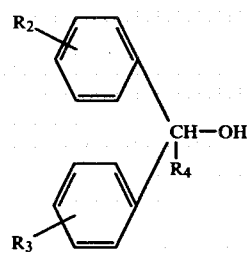
(IX)

or (e) reacting a compound of the formula

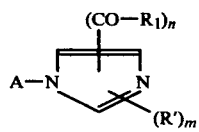
(X)

in which A is a trimethylsilyl or halomagnesium group, with a compound of the formula

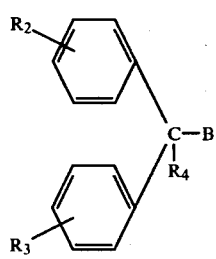
(XI)

in which B is halogen or hydroxy, or (f) oxidizing a compound of the formula

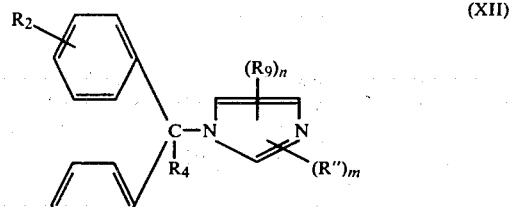
(XII)

in which R" has the same meaning as R except that it is not —SH— or (C$_1$-C$_6$)alkylthio, and R$_9$ is —CH$_2$OH or —CHO, or (g) hydrolizing in a compound of the formula

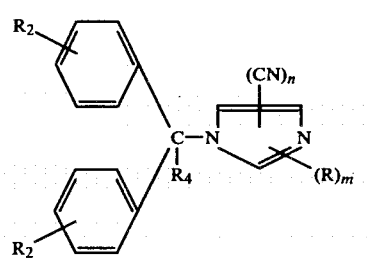
(XIII)

the —CN—group(s) to yield carboxyl group(s) or acide amide group(s) and, if desired, in the compounds obtained by reactions (a) to (g) transesterifying or saponifying the ester groups and/or transforming the free acids obtained into non-phytotoxic salts, esters, thioesters, amides, anilides, or hydrazides and, in the case of several ester groups being present, thermally splitting off one of them.

In the following the manufacturing processes are described in further detail.

(a) The starting compounds of formula III can be prepared by reacting benzhydryl amine with chloroacetic acid ester to yield N-benzhydryl-glycine ester, formylating or acetylating the latter at the nitrogen atom and further reacting the N-acyl compound obtained with formic acid ester (R$_7$=H) or oxalic acid ester (J. Am. Chem. Soc. 71, 644 (1949)). The cyclization with thiocyanic acid takes place smoothly in an inert aqueous system, for example water or a mixture of water and tetrahydrofurane, at temperatures between about 50° C. and the boiling point of the solvent.

In this manner compounds of formula I are obtained which contain hydrogen or a carbalkoxy group in 4-position of the imidazole ring and a —SH—group in 2-position. The latter can be dehydrogenated in known manner, for example by means of iodine, oxygen, hydrogen peroxide or sulfuryl chloride, whereby disulfides of the formula III are obtained.

Alternatively, the SH group can be removed by desulfurization from the compounds obtained in the first place, for example with 15% nitric acid at 30° to 35° C. or with nickel at 50° to 100° C. The desulfurized compounds can then be halogenated or hydroxymethylated in known manner. The hydroxymethyl group can be introduced, for example, by using a formaldehyde solution in methanol or water at elevated temperatures, preferably at 130° to 140° C., in an autoclave.

(b) In this reaction the —CO—R$_8$ group has the function of a protective group to prevent a double reaction at both nitrogen atoms of the imidazole ring. The starting compounds of formula V can be prepared by acylating compounds of the formula VIII at the nitrogen atom 1. The reaction of a compound of the formula V with a compound of the formula VI results in a quaternization at the nitrogen atom 3. The subsequent splitting off of the acyl group by hydrolysis, alcoholysis or aminolysis, which takes place very readily, yields in known manner the desired compounds of the formula I (Rec. Trav. Chim. Pays-Bas 93 (1974), page 56).

In formula VI X stands for a group which makes possible the quaternization of the imidazole ring. A preferred group of this type is halogen (Cl, Br), or an alkyl or arylsulfonyl group (mesyl, tosyl).

The reaction of compound V with compound VI is generally carried out at a temperature of from 60° to 100° C. in a suitable solvent such as acetonitrile or propionitrile.

(c) This reaction corresponds to process (b) with the exception that the second nitrogen atom of the imidazole ring is not protected. In order to avoid a double reaction (especially when Y is hydrogen) it is advantageous to carry out the reaction in the presence of a tertiary amine, for example triethyl amine or N-ethyl-diisopropyl amine in a solvent such as acetonitrile, dimethyl formamide, dimethyl sulfoxide, chloroform, carbon tetrachloride, at a temperature of from 20° to 85° C.

(d) Water is split off according to process (d) preferably at a temperature of from 130° to 150° C. in an inert solvent such as xylene or mesitylene, optionally in the presence of catalytic amounts of aluminium oxide.

(e) The reaction according to (e) takes place at low temperatures in the range of from 0° C. to room temperature or a little thereabove. Preferred solvents are anhydrous benzene, toluene, tetrahydrofurane, or dioxane.

(f) The starting compounds of the formula XII can be prepared according to the process described in J. Am. Chem. Soc. 71 (1949), pages 2801–03, from correspondingly substituted starting compounds. The oxidation is carried out in known manner with a usual oxidation agent, for example potassium permanganate, hydrogen peroxide, chromium trioxide, tert. butyl chromate, nickel peroxide, silver oxide, or manganese dioxide, at a temperature of from 0° to 35° C. Suitable solvents are ketons such as acetone or methyl ethyl ketone, acetic acid, dimethyl sulfoxide and water.

(g) The addition of water to nitrile groups yields either carbonamides or carboxylic acids, depending on the reaction conditions. To obtain carbonamides the components are allowed to react at 20° to 50° C. in about 1 N sodium hydroxide solution, optionally in the presence of catalytic amounts of hydrogen peroxide. Carboxylic acids are obtained by saponifying the nitrile group(s) with about 6 N sodium hydroxide solution at 70° to 100° C. The starting compounds of formula XIII are obtained, for example, according to the process described in Bull. Chem. Soc. Japan 41 (1968), pages 1237–40, from correspondingly substituted starting compounds.

The compounds obtained according to processes (a) to (g) can be modified in many ways at the —CO—$R_1$ group(s). Thus, esters can be saponified in known manner to give the free acids or the salts thereof. The free acids as obtained according to processes (a) to (f) by saponification of ester groups or according to process (g) by hydrolysis of cyano groups can be transformed, optionally via the acid chlorides, into other esters, thioesters, amides, anilides, or hydrazides of the formula —CO—$R_1$. In compounds containing two ester groups one of them can be saponified and decarboxylated. Processes of this type are known to the expert and need not be described in further detail.

The following examples illustrate the invention.

EXAMPLE 1

(a)

1-Benzhydryl-2-mercapto-5-methoxycarbonyl-imidazole 31.3 g (0.1 mol) of 2-benzhydrylformyl)-amino-3-oxo-propionic acid methyl ester (prepared by formylation of (benzhydrylformyl)-aminoacetic acid methyl ester according to J. Am. Chem. Soc. 71, (1949), page 644, and 18 g of potassium thiocyanate were introduced into a mixture of 200 cc of tetrahydrofurane, 200 cc of water and 16.5 cc of 36% aqueous hydrochloric acid while stirring. Stirring was continued for 3½ hours at 40° C.; then the organic phase was separated and the solvent removed under reduced pressure. The residue was taken up in methylene chloride and freed from acid residues by shaking twice with water. After washing with methanol, 29.8 g (92% of the theory) of 1-benzhydryl-2-mercapto-5-methoxy-imidazole melting at 194° C. were obtained.

In analogous manner the following compounds were prepared:

(1b)    1-(4'-chlorodiphenylmethyl)-2-mercapto-5-methoxycarbonyl-imidazole, m.p. 184° C.;

(1c)    1-(4'.methyldiphenylmethyl)-2-mercapto-5-methoxycarbonyl-imidazole, m.p. 186° C.

EXAMPLE 2

(a) 1-Benzhydryl-2-mercapto-5-imidazole-carboxylic acid 3.2 g (0.01 mol) of 1-benzhydryl-2-mercapto-5-methoxycarbonyl-imidazole (Example 1a) and 20 cc of 1 N sodium hydroxide solution were heated for 3 hours to 80° C. whereby the disodium salt of 1-benzhydryl-2-mercapto-5-imidazole-carboxylic acid was obtained in practically quantitative yield (3.5 g). The salt decomposed at a temperature above 255° C. Crystalline 1-benzhydryl-2-mercapto-5-imidazole-carboxylic acid, m.p. 158° C., was obtained by dissolving the salt in water and acidifying the solution with 2 N hydrochloric acid.

In an analogous manner the following compounds were prepared:

(2b)    1-(4'-chlorodiphenylmethyl)-2-mercapto-5-imidazolecarboxylic acid, m.p. 153° C.;

(2c)    1-(4'-methyldiphenylmethyl)-2-mercapto-5-imidazolecarboxylic acid, m.p. 140° C.

EXAMPLE 3

(a)

1-Benzhydryl-2-mercapto-5-propoxycarbonyl-imidazole 3.1 g (0.01 mol) of 1-benzhydryl-2-mercapto-5-imidazole carboxylic acid (Example 2a) and 100 cc of 1-propanol were heated to 97° C. while introducing gaseous hydrogen chloride until esterification was completed. Working up in a basic medium yielded 3.3 g (94% of the theory) of 1-benzhydryl-2-mercapto-5-propoxycarbonyl-imidazole, m.p. 133° C.

In analogous manner the following compound was prepared:

(3b) 1-benzhydryl-2-mercapto-5-ethoxycarbonyl-imidazole, m.p. 194° C.

EXAMPLE 4

1-Benzhydryl-5-methoxycarbonyl-2-methylthio-imidazole 3.2 g (0.01 mol) of 1-benzhydryl-2-mercapto-5-methoxycarbonyl-imidazole (Example 1a) were introduced into a mixture of 30 cc of water, 15 cc of methanol, 15 cc of methylene chloride, 10 cc of 2 N sodium hydroxide solution and 1.3 cc of methyl iodide. Stirring was continued for 30 minutes. During this time the temperature of the reaction mixture rose to 39° C. After cooling, 3 g (90% of the theory) of 1-benzhydryl-5-methoxycarbonyl-2-methylthio-imidazole, m.p. 118° C. were isolated from the organic phase.

EXAMPLE 5

1-Benzhydryl-2-mercapto-5-imidazole-carboxylic acid pyrrolidide

In a nitrogen atmosphere 3.2 g (0.01 mol) of 1-benzhydryl-2-mercapto-5-methoxycarbonyl-imidazole (Example 1a) and 60 cc of pyrrolidine were refluxed for 3 days. Excess pyrrolidine was then removed in vacuo and the 1-benzhydryl-2-mercapto-5-imidazole-carboxylic acid pyrrolidine obtained was recrystallized from methanol (m.p. 263° C.). The yield was 3.3 g (91% of the theory).

EXAMPLE 6

Bis(1-benzhydryl-5-methoxycarbonyl-imidazolyl(2))-disulfide

A 10% aqueous potassium iodide-iodine solution was added to a solution of 3.2 g (0.01 mol) of 1-benzhydryl-2-mercapto-5-methoxycarbonyl-imidazole (Example 1a) in 60 cc of 2 N sodium hydroxide solution until the precipitate formation was completed. The precipitate was isolated, washed with water and transferred into a separating funnel containing 250 cc of carbon tetrachloride and 50 cc of a 5% aqueous sodium hydrogen sulfite solution. The organic phase was separated, dried and concentrated, yielding 3.0 g (95% of the theory) of bis(1-benzhydryl-5-methoxycarbonyl-imidazolyl(2))-disulfide in crystalline form, m.p. 154° C.

EXAMPLE 7

Bis(1-benzhydryl-5-carboxyl-imidazolyl(2))-disulfide 3.2 g (0.005 mol) of bis(1-benzhydryl-5-methoxycarbonyl-imidazolyl(2))-disulfide (Example 6) were saponified at 80° C. with the equivalent amount of 2 N sodium hydroxide solution. The cooled reaction mixture was acidified with hydrochloric acid, 3.0 g (96% of the theory) of bis(1-benzhydryl-5-carboxyl-imidazolyl(2))-disulfide, m.p. 180° C. with decomposition were obtained.

EXAMPLE 8

(a) 1-Benzhydryl-5-methoxycarbonyl-imidazole 325 cc of 15% nitric acid and 1.6 g of sodium nitrite were added while stirring to 325 cc of methylene chloride. 32.5 g (0.1 mol) of 1-benzhydryl-2-mercapto-5-methoxycarbonyl-imidazole (Example 1a) were then added in portions at 35° C. while stirring. Stirring at 35° C. was continued for a further 30 minutes, the reaction mixture was cooled to 10° C. and the crystallized 1-benzhydryl-5-methoxycarbonyl-imidazole nitrate was filtered off with suction. The crystals were freed from acid residues by means of ice water and dried under reduced pressure at 30° C., m.p. 175° C. with decomposition.

From the washed and neutralized methylene chloride phase 9.2 g (32% of the theory) of 1-benzhydryl-5-methoxycarbonyl-imidazole, melting at 129° C., were obtained.

For transformation into the free base the nitrate was suspended in 100 cc of chloroform and the total amount of the nitrate was dissolved by adding about 60 cc of 1 N sodium hydroxide solution. From the chloroform solution 17.8 g (61% of the theory) of 1-benzhydryl-5-methoxycarbonyl-imidazole were isolated.

In analogous manner the following compounds were prepared from 1-(4-chlorodiphenylmethyl)-2-mercapto-5-methoxycarbonyl imidazole (Example 1b):

(8b) 1-(4'-chlorodiphenylmethyl)-5-methoxycarbonyl-imidazole, m.p. 94° C.;

(8c) 1-(4'-methyldiphenylmethyl)-5-methoxycarbonyl-imidazole, m.p. 85° C.

EXAMPLE 9

1-Benzhydryl-5-methoxycarbonyl-imidazole hydrochloride 1 g of 1-benzhydryl-5-methoxycarbonyl-imidazole (Example 8) was dissolved in 45 cc of diethyl ether. The 1-benzhydryl-5-methoxycarbonyl-imidazole hydrochloride was obtained by adding ethereal hydrochloric acid. The compound melted at 136° C.

EXAMPLE 10

1-Benzhydryl-2-hydroxymethyl-5-methoxycarbonyl-imidazole 2.9 g (0.01 mol) of 1-benzhydryl-5-methoxycarbonyl-imidazole (Example 8) and 25 cc of 50% methanolic formaldehyde solution were heated for 36 hours to 135° C. 3.15 g of 1-benzhydryl-2-hydroxymethyl-5-methoxycarbonyl-imidazole, m.p. 160° C., were obtained from the reaction mixture in an almost quantitative yield.

EXAMPLE 11

(a) 1-Benzhydryl-5-imidazole-carboxylic acid 2.9 g (0.01 mol) of 1-benzhydryl-5-methoxycarbonyl-imidazole (Example 8) were saponified at 80° C. with an equivalent amount of 1 N sodium hydroxide solution. The sodium salt of 1-benzhydryl-5-imidazole-carboxylic acid obtained melted at 176° C. The desired 1-benzhydryl-5-imidazole-carboxylic acid, m.p. 216° C., was obtained by acidifying the aqueous solution of the sodium salt with hydrochloric acid. Yield 2.64 g (95% of the theory).

The following compounds were prepared in an analogous manner from 1-(4'-chlorodiphenylmethyl)-5-methoxycarbonyl-imidazole (according to Example 6b):

(11b) 1-(4'-chlorodiphenylmethyl)-5-imidazole-carboxylic acid, m.p. 135° C.;

(11c) 1-(4'-methyldiphenylmethyl)-5-imidazole-carboxylic acid, m.p. 202° C.

The following compounds were prepared from the dried sodium salt of 1-benzhydryl-5-imidazole-carboxylic acid (Example 11a):

(11d) 1-benzhydryl-5-n-butoxycarbonyl-imidazole, m.p. 53° C. by reaction with n-butyl bromide;
(11e) 1-benzhydryl-5-benzyloxycarbonyl-imidazole, m.p. 104° C. by reaction with benzyl chloride.

EXAMPLE 12

(a) 1-Benzhydryl-5-propoxycarbonyl-imidazole

Gaseous hydrochloric acid was introduced into 2.8 g (0.01 mol) of 1-benzhydryl-5-imidazole carboxylic acid (according to Example 11) in 140 cc of 1-propanol while refluxing the mixture until the esterification was completed. The hydrochloride formed was neutralized and yielded 3.1 g (96% of the theory) of 1-benzhydryl-5-propoxycarbonyl-imidazole, m.p. 81° C.

The following compounds were prepared in analogous manner:
(12b) 1-benzhydryl-5-ethoxycarbonyl-imidazole, m.p. 92° C.;
(12c) 1-benzhydryl-5-butoxycarbonyl-imidazole, m.p. 53° C.;
(12d) 1-benzhydryl-5-benzoyloxycarbonyl-imidazole, m.p. 104° C.

EXAMPLE 13

1-Benzhydryl-5-propoxycarbonyl-imidazole

The compound was prepared by transesterification of 2.9 g (0.01 mol) of 1-benzhydryl-5-methoxycarbonyl-imidazole of Example 8. To this end it was refluxed for some time in 100 cc of propanol and in the presence of catalytic amounts of toluene sulfonic acid. The colorless crystals obtained had a melting point of 81° C.

EXAMPLE 14

(a) 1-benzhydryl-5-(dimethylphosphinylmethoxycarbonyl)-imidazole 3.0 g (0.01 mol) of the sodium salt of 1-benzhydryl-5-imidazole-carboxylic acid (Example 11) and 1.8 g of chloromethyl dimethyl phosphine oxide were heated with 40 cc of dimethyl formamide to 120° C. under a nitrogen atmosphere until the reaction was completed. The solvent was removed under reduced presure and insoluble sodium chloride was separated by taking up the residue in acetone. Crystallization yielded colorless crystals melting at 174° C., Yield 3.2 g (88% of the theory).

The following compounds were prepared in analogous manner:
(14b) 1-benzhydryl-5-(3-(dimethylphosphinyl)-propoxycarbonyl)-imidazole, m.p. 78° C., with the use of 3-chloropropyl dimethyl phosphine oxide;
(14c) 1-benzhydryl-5-(2-dimethylphosphinyl-2-hydroxyethoxycarbonyl)-imidazole, m.p. 197° C., with the use of 1-dimethylphosphinyl 2-chloroethanol; and
(14d) 1-benzhydryl-5-(2-dimethylphosphinyl-2-hydroxypropoxy-carbonyl)-imidazole, m.p. 89° C., with the use of 2-dimethylphosphinyl 1-chloropropanol(2).

EXAMPLE 15

(a) 1-Benzhydryl-5-hydrazinocarbonyl-imidazole 2.9 g (0.01 mol) of 1-benzhydryl-5-methoxycarbonyl-imidazole (Example 8) in 10 cc of methanol and 0.8 cc of hydrazine hydrate were refluxed for some time. After cooling, 2.9 g of benzhydryl-5-hydrazinocarbonyl-imidazole, melting at 152° C. were isolated.

The following compounds were prepared in analogous manner:
(15b) 1-benzhydryl-5-(N',N'-dimethylhydrazinocarbonyl)-imidazole, m.p. 211° C.;
(15c) 1-benzhydryl-5-(N'-methylhydrazinocarbonyl)-imidazole, m.p. 123° C.;
(15d) 1-benzhydryl-5-hydrazinocarbonyl-2-mercapto-imidazole, m.p. 222° C.

EXAMPLE 16

(a) Benzhydryl-5-imidazole-carboxylic acid pyrrolidide 2.9 g (0.01 mol) of 1-benzhydryl-5-methoxycarbonyl-imidazole (Example 8) in 15 cc of pyrrolidine were refluxed for 6 hours. Excess pyrrolidine was removed in vacuo and the residue dissolved in methylene chloride. By means of a silica gel column the 1-benzhydryl-5-imidazol-carboxylic acid pyrrolidide was freed from colored impurities. Yield 2.8 g (86% of the theory), m.p. 117° C.

The following compound was obtained in analogous manner:
(16b) 1-benzhydryl-5-(2'-diethylaminoethylaminocarbonyl)-imidazole monohydrate, m.p. 60° C.

EXAMPLE 17

(a) 1-Benzhydryl-5-imidazole carboxylic acid amide

In an autoclave 2.9 g (0.01 mol) of 1-benzhydryl-5-methoxy-carbonyl-imidazole and 300 cc of methanolic ammonia solution, saturated at 20° C., were heated for 8 hours to 120° C. 2.7 g (96% of the theory) of 1-benzhydryl-5-imidazole-carboxylic acid amide, m.p. 153° C., were obtained.

The following compound was prepared in analogous manner:
(17b) 1-benzhydryl-2-mercapto-5-imidazole-carboxylic acid amide, m.p. 131° C.

EXAMPLE 18

1-Benzhydryl-2-mercapto-4,5-dimethoxycarbonyl-imidazole

In the manner described in Example (1a) 36.9 g (0.01 mol) of 2-(benzhydrylformyl)-amino-3-oxo-succinic acid dimethyl ester (prepared by reacting (benzhydrylformyl)-aminoacetic acid methyl ester with oxalic acid dimethyl ester in the presence of sodium methylate) were reacted with 18 g of potassium thiocyanate for 48 hours at 50° C. The 1-benzhydryl-2-mercapto-4,5-dimethoxycarbonyl-imidazole formed crystallized on adding hexane. Yield 33.2 g (87% of the theory), m.p. 154° C.

EXAMPLE 19

1-Benzhydryl-4,5-dimethoxycarbonyl-imidazole 3.8 g (0.01 mol) of 1-benzhydryl-2-mercapto-4,5-dimethoxy-carbonyl-imidazole (Example 17) in 50 cc of methanol were refluxed for 4 hours in the presence of 400 mg of Raney nickel. The catalyst was separated and thoroughly washed with methanol. The combined filtrate were concentrated and 3.1 g (90% of the theory) of 1-benzhydryl-4,5-dimethoxy-carbonyl-imidazole, m.p. 93° C., were obtained.

EXAMPLE 20

(a) 1-Benzhydryl-4,5-dimethoxycarbonyl-imidazole 20.3 g of benzhydryl chloride were added dropwise to a suspension of 18.4 g (0.1 mol) of 4,5-dimethoxycarbonyl-imidazole in 60 cc of acetonitrile and 14 cc of triethylamine and the reaction mixture was heated for 8 hours at 80° C. The solvent was then removed under reduced pressure and triethylammonium chloride was separated by washing with water. 30 g (85% of the theory) of 1-benzhydryl-4,5-dimethoxycarbonyl-imidazole, m.p. 93° C., were obtained.

The following compound was obtained in analogous manner with the use of 2-chlorotrityl chloride (=2-chlorotriphenylmethyl chloride):
(20b)  1-(2'-chlorotrityl)-4,5-dimethoxycarbonyl-imidazole, m.p. 202° C.

EXAMPLE 21

Potassium salt of 1-benzhydryl-2-imidazole-carboxylic acid 2.64 g (0.01 mol) of 1-benzhydryl-2-hydroxymethyl-imidazole, m.p. 174° C. (prepared from 1-benzhydryl-imidazole and formaldehyde), were dissolved in 150 ml of acetone. While stirring at 5° C. a solution of 1.7 g of potassium permanganate in 120 cc of acetone was added dropwise. After 2 hours the solvent was removed under reduced pressure, the residue was stirred with 150 cc of chloroform and 150 cc of water and the separated manganese dioxide was filtered off. Crystalline potassium salt of 1-benzhydryl-2-imidazole-carboxylic acid was obtained from the chloroform phase. The salt decomposed at a temperature above 280° C.

1-Benzhydryl-2-imidazole-carboxylic acid

The potassium salt obtained according to Example 20 was stirred with 0.1 N hydrochloric acid yielding fine needles of 1-benzhydryl-2-imidazole-carboxylic acid, m.p. 191° C. (about 70% of the theory).

EXAMPLE 22

1-Benzhydryl-5-methoxycarbonyl-imidazole 1.7 g (0.01 mol) of 1-acetyl-4-methoxycarbonyl-imidazole in 5 cc of acetonitrile and 2 g of benzhydryl-chloride were refluxed for 4 hours, the solvent was removed under reduced pressure and the residue was stirred with 15 cc of 0.5 N sodium acetate solution to split off the acetyl group. The 1-benzhydryl-5-methoxycarbonyl-imidazole, m.p. 129° C., was recrystallized from chloroform.

EXAMPLE 23

(a) 1-Benzhydryl-4,5-imidazole-dicarboxylic acid 2.9 g (0.01 mol) of 1-benzhydryl-4,5-imidazole-dinitrile were thoroughly saponified with an equivalent amount of 3 N sodium hydroxide solution. On acidification of the solution 2.7 g (85% of the theory) of 1-benzhydryl-4,5-imidazole-dicarboxylic acid, m.p. 194° C., were obtained.

(23b) In an analogous manner 1-(2'-chlorotrityl)-4,5-imidazole-dinitrile, m.p. 270° C. (with decomposition), was obtained from 1-(2'-chlorotrityl)-4,5-imidazole-dicarboxylic acid.

EXAMPLE 24

1-Benzhydryl-5-methylthiocarbonyl-imidazole 2.8 g (0.01 mol) of 1-benzhydryl-5-imidazole-carboxylic acid were transformed at 40° C. with 4.5 cc of thionyl chloride into the hydrochloride of 1-benzhydryl-5-imidazole-carboxylic acid chloride, which was freed from residual thionyl chloride with the aid of methylene chloride. The crystalline hydrochloride was dissolved in 20 cc of tetrahydrofurane and was reacted overnight at 25° C. with 1.4 g (0.02 mol) of sodium methylmercaptide while stirring. The solvent was removed under reduced pressure and replaced by 50 cc of methylene chloride. The solution of the thiomethyl ester was separated from the insoluble sodium chloride. When worked up with pentane the ester obtained from the solution in the form of an oily residue separated in crystal form. The 1-benzhydryl-5-methylthiocarbonyl-imidazole was obtained in a yield of 85% and had a melting point of 98° C.

The following compounds were obtained in analogous manner from 1-benzhydryl-5-imidazole-carboxylic acid chloride hydrochloride:
(24b) by reaction with sodium 2-methoxyethylate and subsequent acidification with HCl: 1-benzhydryl-5-(2-methoxyethoxy)-carbonyl-imidazole hydrochloride, m.p. 125° C.;
(24c) by reaction with hydroxyl amine hydrochloride and triethyl amine: 1-benzhydryl-5-hydroxyaminocarbonyl-imidazole, m.p. 93° C.;
(24d) by reaction with diethylamino-ethylamino hydrochloride and triethylamine: 1-benzhydryl-5-(2-diethylamino-ethylamino)-carbonyl-imidazole monohydrate, m.p. 60° C.;
(24e) by reaction with sodium propyl mercaptide and acidification with HCl: 1-benzhydryl-5-n-propylthiocarbonyl-imidazole-hydrochloride, m.p. 140° C.

EXAMPLE 25

1-Benzhydryl-2-(4)-bromo-5-methoxycarbonyl-imidazole

A solution of 1.6 g of bromine in 5 cc of carbon tetrachloride was added while stirring to 2.9 g (0.01 mol) of 1-benzhydryl-5-methoxycarbonyl-imidazole and 1.4 g of finely pulverized potassium carbonate in 60 cc of carbon tetrachloride. The reaction mixture was refluxed for 6 hours, allowed to cool and the solution was decanted from the separated potassium bromide. The solvent was then replaced by 15 cc of diisopropyl ether and the 1-benzhydryl-2-(4)-bromo-5-methoxycarbonyl-imidazole was isolated in the form of slightly yellow crystals, m.p. 78° C. Yield 3.0 g (82% of the theory).

The compounds according to the invention can be used for various purposes in agriculture and horticulture. They are effective growth regulators, herbicides and fungicides. They can also be used for the control of moss, of plant-pathogenic bacteria and as antimycotics.

The invention, therefore, also provides compositions to be used in agriculture and horticulture and as antimycotics, plant growth regulators and herbicides as well as for combating fungi and plant-pathogenic bacteria.

For the manufacture of the compositions the active compounds of the invention are formulated in usual manner, either alone or in combination with other active compounds or fertilizers, to give powders, dusts, pastes, granules, solutions, foams, emulsions, and suspensions. For blending and diluting the active compounds solvents, liquefied gases, emulsifiers, dispersants, foam producing agents and solid carrier materials as known in the production of plant protecting agents can be used.

The compounds of the invention can be applied in a wide concentration range of from about 0.00005 to 2%. In special cases they can be used in a higher concentration and even in the pure state, for example ground to microfine particles. When used as herbicides or growth regulators the concentration of active substance generally ranges from 0.01 to 5 kg per hectare. The active compounds of the invention are preferably used in the form of 20 to 50% wettable powders containing the usual proportions of inert substances, dispersing agents, wetting agents and optionally adhesives; 15 to 30% emulsion concentrates, and 5% granules as well as dusts of varying concentration of active compound. Compositions for the treatment of mycoses of the skin generally contain from 0.5 to 2% of active compound.

When used as growth regulators the compounds of the invention exhibit an excellent growth-retarding efficiency, for example in cereals, horse beans and lawns and in the germination test of linseed and oat.

With the use of growth regulators the harvest can be facilitated and the crop yield increased while simultaneously the quality of the harvested crops is improved. By shortening and strengthening the stems of cereals the nutrient supply of the spikes is improved and storage losses can be reduced. Moreover, by the use of growth regulators the protein content in cereals and soybeans and the sugar content in sugar beets and sugar cane can be increased. Further fields of application are, for example, the optimization of the propagation by cuttings and of the leaf growth of tobacco plants. The growth of grass, herbs and bushes can be controlled so that the cultivation costs can be reduced. In special cases the use of mechanical harvest aids becomes possible by the use of growth regulators or the costs thereof are at least reduced. In the cultivation of ornamental plants the growth can be adpated to the qualitative and seasonal demands of the market.

The compounds of the invention are further characterized by very good herbicidal properties, especially in pre-emergence application, against a large number of economically important weed grasses and dicotyledonous weeds. On the other hand, they are tolerated by some crop cultures such as cotton, maize, rape, and beans, and hence can be used in selective weed control.

Still further, the compounds of the invention have an excellent and in some cases even systemic effect against phytopathogenic fungi and, hence are suitable for plant protection. They exhibit e.g. a good fungicidal effect against rust fungi, *Phytophthora infestans*, *Plasmopara viticola*, *Venturia inaequalis*, *Phoma betae* and *Botrytis cinerea* and also against skin fungi such as *Trichophyton mentagrophytes* and *Microsporium canis*. Particularly good is the fungicidal effect of the compounds against *Piricularia oryzae* and genuine types of mildew in cucumber, cereals (wheat and barley), apples and ornamental plants, and more especially against benzimidazole-resistant types of mildew.

The fungicidal compositions can be formulated in usual manner, for example as dusts, wettable powders, dispersions, and emulsifiable concentrates. They preferably contain from 10 to 90% by weight of active matter in addition to the usual adhesives, wetting agents, dispersants, fillers, and carrier materials.

EXAMPLE I (growth inhibition)

Young plants of cereals in the three-leaf stage were sprayed to the drip off with preparations of active compounds. When the untreated control plants had grown to a height of about 55 cm, the growth increase of all plants was measured and the inhibition of growth was calculated in percent of the increase in length of the control plants. The results are listed in the following Table I. 100% means total stagnation of growth and 0% indicates a growth corresponding to that of the untreated control plants, i.e. no inhibition.

TABLE I

| compound of Example | Inhibition of growth in cereals | | | |
|---|---|---|---|---|
| | concentration (kg/ha) | inhibition of growth in % | | |
| | | wheat | barley | rye |
| 6 | 2.5 | 25 | 28 | 40 |
| | 1.25 | 20 | 15 | 31 |
| 8 a | 2.5 | 41 | 36 | 42 |
| | 1.25 | 32 | 31 | 37 |
| comparison (2-chloroethyl)-tri-methyl-ammonium chloride | 2.5 | 31 | 10 | 10 |
| | 1.25 | 28 | 0 | 0 |

EXAMPLE II (herbicidal effect)

Weeds of several botanic families were sown in pots and treated in the pre-emergence process with compounds of the invention. The weeds were allowed to germinate and grow in the greenhouse. About 4 weeks after treatment the result was evaluated visually by the scheme according to Bolle (Table II). It can be seen that the tested compounds had a vey good effect against numerous weeds.

TABLE II

| Evaluation scheme according to Bolle (Nachrichtenblatt des Deutschen Pflanzenschutzdienstes 16, 1964, 92–94) | | | | | |
|---|---|---|---|---|---|
| evaluation number | Damage in % in | | | | |
| | weeds | | | crop plants | |
| 1 | | 100 | | | 0 |
| 2 | 97.5 | to | 100 | 0 to | 2.5 |
| 3 | 95 | " | 97.5 | 2.5 " | 5 |
| 4 | 90 | " | 95 | 10 " | 15 |
| 5 | 85 | " | 90 | 15 " | 25 |
| 6 | 75 | " | 85 | 15 " | 25 |
| 7 | 65 | " | 75 | 25 " | 35 |
| 8 | 32.5 | " | 65 | 35 " | 67.5 |
| 9 | 0 | " | 32.5 | 67.5 " | 100 |

The results of the visual evaluation are summarized in the following Tables III and IV.

TABLE III

| Biological effect against important monocotyledonous and dicotyledonous weeds in a pre-emergence trial | | | | | | | | | | | | |
|---|---|---|---|---|---|---|---|---|---|---|---|---|
| Compound of Ex. | dose (kg AS/ha) | type of plant | | | | | | | | | | |
| | | 1 | 2 | 3 | 4 | 5 | 6 | 7 | 8 | 9 | 10 | 11 |
| 1 a | 2.5 | — | 3 | 1 | 1 | 1 | 1 | 1 | 1 | 3 | 1 | 1 |
| | 0.6 | — | 4 | 1 | 1 | 2 | 1 | 1 | 1 | 4 | 1 | 1 |
| 8 a | 2.5 | 4 | 2 | 1 | 1 | 1 | 2 | 1 | 1 | 3 | 1 | 1 |
| | 0.6 | 4 | 2 | 1 | 1 | 1 | 2 | 1 | 1 | 3 | 1 | 1 |
| 6 | 2.5 | — | 2 | 1 | 1 | 2 | 2 | 1 | 1 | — | 1 | 1 |
| | 0.6 | — | 3 | 1 | 1 | 3 | 5 | 1 | 1 | — | 4 | 1 | legend:
1 Avena
2 Alopecurus
3 Setaria
4 Poa
5 Cyperus
6 Lolium
7 Digitaria
8 Echinochloa
9 Chrysanthemum
10 Stellaria
11 Amaranthus
AS = active substance

EXAMPLE III (fungicidal effect)

In the following examples the letters A to E indicate the following comparative compounds:

A: methyl-1-(butylcarbamoyl)-2-benzimidazole carbamate (Benomyl)
B: N-tridecyl-2,6-dimethyl-morpholine (Tridemorph)
C: 2,4-dinitro-6-sec. butyl-phenyl-3,3-dimethyl-acrylate (Binapacryl)
D: O-ethyl-S,S-diphenyl-dithio-phosphate (Edifenfos)
E: Polyoxine Wheat plants in the three-leaf stage were strongly infested with conidia of wheat mildew (*Erysiphe graminis*) and kept in a greenhouse at 20° C. and a relative humidity of 90 to 95%. In the same manner cucumber plants in the two-leaf stage and rice plants in the four-leaf stage were infested with conidia of *Erysiphe cichoracearum* (cucumber mildew) and *Piricularia oryzae*, respectively. 3 Days after infestation, the plants were sprayed to the drip off with compounds of the invention in different concentrations. As comparative agents compounds A and B were used in the same concentrations. After a time of incubation of 10 to 14 days, the plants were examined as to their infestation with fungi. The degree of infestation is expressed in the following table IV in % of infested leaf surface, calculated on untreated and infested control plants (=100%).

TABLE IV

| | | Effect against phytopathogenic fungi | | |
| | | infested leaf surface in % when applied against | | |
| Compound of Example | concentration (mg of AS per liter of spray liquor) | Erysiphe graminis (wheat) | Erysiphe cichoracearum (cucumber) | Piricularia oryzae (rice) |
| --- | --- | --- | --- | --- |
| | 250 | 0 | 0 | — |
| 1 a | 125 | 0 | 0 | — |
| | 250 | — | 0 | — |
| 2 a (Na-salt) | 125 | — | 0 | — |
| | 250 | 0-3 | 0 | — |
| 6 | 125 | 3 | 0 | — |
| | 250 | 0-3 | 0 | 0-3 |
| 8 a | 125 | 3 | 0 | 3 |
| A | 250 | 5 | 5 | — |
| | 125 | 10 | 10 | — |
| B | 250 | 5 | — | — |
| | 125 | 10 | — | — |
| C | 250 | — | 5 | — |
| | 125 | — | 15 | — |
| D | 250 | — | — | phytotoxic burnings |
| | 125 | — | — | |
| E | 250 | — | — | 15 |
| | 125 | — | — | 25 |
| untreated infested plants | | 100 | 100 | 100 |

EXAMPLE IV (bactericidal effect)

In Petri dishes 0.02 cc each of a bacterium suspension of *Xanthomonas malvacearum* and *Corynebacterium michiganense* was dropped on the center of a culture agar for bacteria, which culture had previously been admixed while still liquid with the compounds listed in Table V in different concentrations. The inoculated agar plates were evaluated after 4 days and the growth inhibition was determined in % in comparison with control plates (infested agar without addition of active substance (0% inhibition).

TABLE V

| | | Bactericidal effect | |
| Compound of Example | concentration ppm | Xanthomonas malvacearum (gram-negative) | Corynebacterium michinanense (gram-positive) |
| --- | --- | --- | --- |
| 11 a (Na-salt) | 250 | 97 | 95 |
| | 125 | 70 | 50 |
| 12 a | 250 | 97 | — |
| | 125 | 80 | — |
| 1 a | 250 | — | 100 |
| | 125 | — | 100 |
| 11 a (acid) | 250 | — | 100 |
| | 125 | — | 100 |

What is claimed is:

1. Imidazole-carboxylic acids and their derivatives of formulae

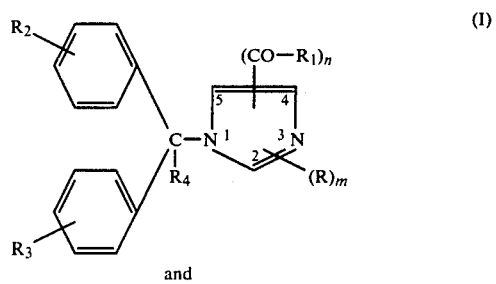

and

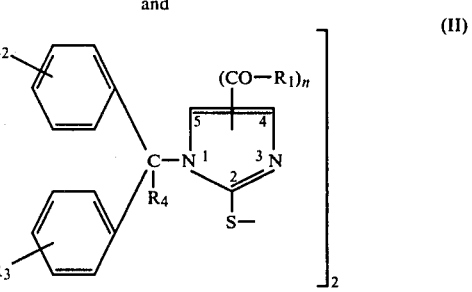

in which
m is zero, 1 or 2,
n is 1 or 2, and
m+n is equal to or smaller than 3;
R is halogen, $(C_1-C_6)$alkyl, allyl, hydroxy$(C_1-C_6)$alkyl, halo$(C_1-C_6)$alkyl, thiol, $(C_1-C_6)$alkylthio, cyano, phenyl or phenyl$(C_1-C_2)$alkyl;
$R_1$ is hydroxy, $(C_1-C_6)$alkoxy, hydroxy$(C_2-C_6)$alkoxy, $(C_2-C_6)$alkoxyalkoxy, di$(C_1-C_3)$alkylphosphinyl-$(C_1-C_3)$-alkoxy, di$(C_1-C_3)$alkylphosphinyl-$(C_2-C_3)$hydroxyalkoxy, amino, $(C_1-C_6)$alkylamino, di$(C_1-C_6)$alkylamino, di$(C_1-C_3)$ alkylamino-$(C_1-C_3)$alkylamino, hydroxyamino, $(C_1-C_3)$alkoxyamino; N-$(C_1-C_3)$-alkyl-N-$(C_1-C_3)$-alkoxyamino, anilino, N-pyrrolidino, N-piperidino, N-morpholino, hydrazino, N'-$(C_1-C_3)$-alkylhydrazino, N',N'-dimethylhydrazino or N'-phenylhydrazino;
$R_2$ and $R_3$, which can be identical or different, are hydrogen, halogen, $(C_1-C_3)$alkyl, trifluoromethyl, hydroxy, $(C_1-C_3)$alkoxy, halo-$(C_1-C_3)$alkoxy, $(C_1-C_3)$alkylthio, cyano, nitro or acetamino, and
$R_4$ is hydrogen or phenyl,
and the non-toxic salts thereof with acids or bases.

2. A compound as claimed in claim 1 having the formula

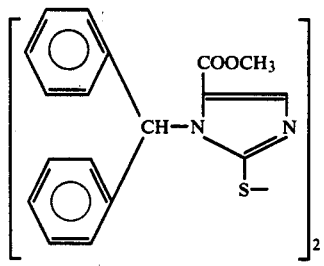

3. A compound as claimed in claim 1 having the formula

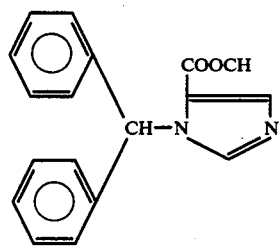

4. A compound as claimed in claim 1 having the formula

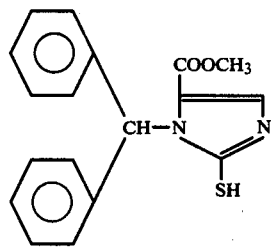

5. A compound as claimed in claim 1 having the formula

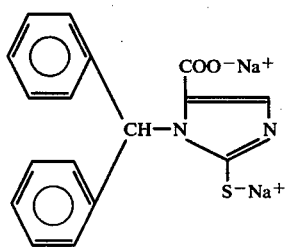

6. A compound as claimed in claim 1 having the formula

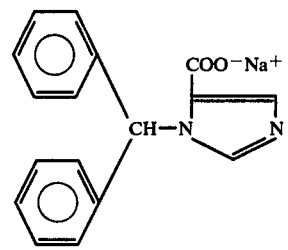

7. A compound as claimed in claim 1 having the formula

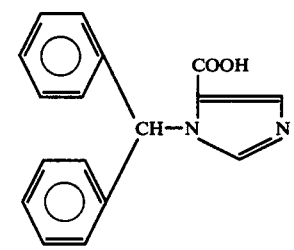

8. A compound as claimed in claim 1 having the formula

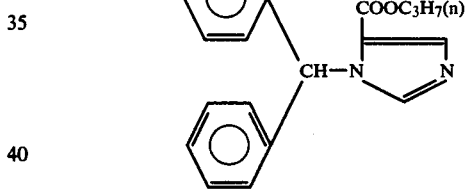

9. A plant growth regulating composition containing a growth-regulating amount of a compound as claimed in claim 1.

10. A composition for combating fungi and plant-pathogenic bacteria in plants, said composition containing an anti-fungi and anti-plant pathogen effective amount of a compound as claimed in claim 1.

11. A method of controlling plant growth which comprises applying to the plants a growth regulating amount of a compound as claimed in claim 1.

12. A method combating fungi and plant-pathogenic bacteria on plants which comprises applying to said plants an anti-fungi and anti-plant pathogen effective amount of a compound as claimed in claim 1.

* * * * *